United States Patent
Schumacher et al.

(10) Patent No.: US 6,666,208 B1
(45) Date of Patent: Dec. 23, 2003

(54) SET FOR INSERTING A SHUNT VALVE INTO A SHUNT BETWEEN THE OESOPHAGUS AND THE TRACHEA

(75) Inventors: Erhard Schumacher, Winkel (DE); Thomas Schultz, Adendorf (DE)

(73) Assignee: Adeva Medical Gesellschaft fur Entwicklung und Vertrieb Von Medizinischen Implantat-Artikeln mbH (DE)

(*) Notice: Subject to any disclaimer, the term of this patent is extended or adjusted under 35 U.S.C. 154(b) by 0 days.

(21) Appl. No.: 09/787,470

(22) PCT Filed: Sep. 16, 1999

(86) PCT No.: PCT/EP99/06853
§ 371 (c)(1),
(2), (4) Date: Mar. 16, 2001

(87) PCT Pub. No.: WO00/16720
PCT Pub. Date: Mar. 30, 2000

(30) Foreign Application Priority Data

Sep. 17, 1998 (DE) .......................................... 198 42 505
Nov. 9, 1998 (DE) ..................................... 298 19 974 U

(51) Int. Cl.[7] ................................................. A62B 9/00
(52) U.S. Cl. ..................................... 128/200.24; 604/9
(58) Field of Search ..................... 128/200.24, 203.12, 128/204.18, 200.26, 205.24, 207.14–207.18; 606/108, 116; 604/116, 8–10; 623/9, 14.11

(56) References Cited

U.S. PATENT DOCUMENTS

| | | | | |
|---|---|---|---|---|
| 3,707,301 A | * | 12/1972 | Rauls | 128/207.18 |
| 4,808,183 A | | 2/1989 | Panje | |
| 5,058,580 A | * | 10/1991 | Hazard | 128/207.15 |
| 5,300,119 A | | 4/1994 | Blom | |
| 5,681,323 A | * | 10/1997 | Arick | 606/108 |

FOREIGN PATENT DOCUMENTS

| | | |
|---|---|---|
| EP | 0 551 198 | 7/1993 |
| WO | WO 95 29649 | 11/1995 |
| WO | WO 96 35399 | 11/1996 |
| WO | WO 97 23341 | 7/1997 |

* cited by examiner

*Primary Examiner*—Glenn K. Dawson
(74) *Attorney, Agent, or Firm*—Cantor Colburn LLP

(57) ABSTRACT

The invention relates to a set for inserting a shunt valve into a surgically produced connecting channel between the trachea and the oesophagus of a laryngectomee. The shunt valve has at least two flexible, rolled up fixing strips at the oesophagus end. The fixing straps can be unrolled after introduction into the connecting channel and then rest against the oesophagus wall. The set has a support with a proximal, essentially cylindrical coupling piece on which the shunt valve is placed, and a holding and releasing element, which releasably holds the at least two fixing straps in their rolled-up position and releases them when activated.

3 Claims, 3 Drawing Sheets

Figure 3:
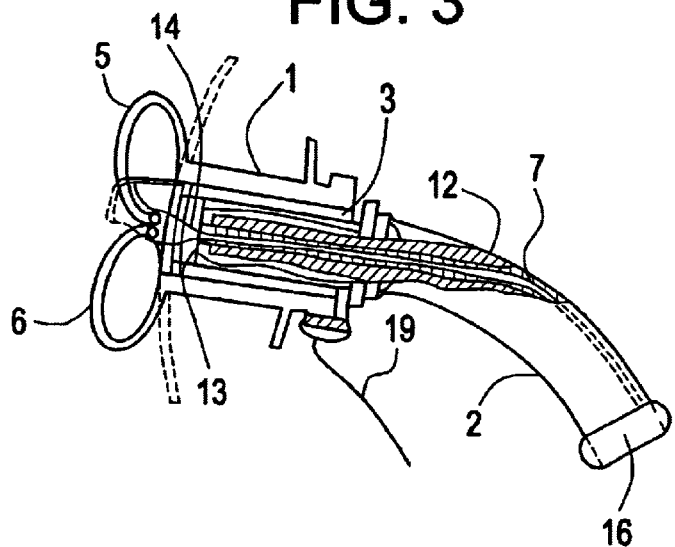

FIG. 1
FIG. 2
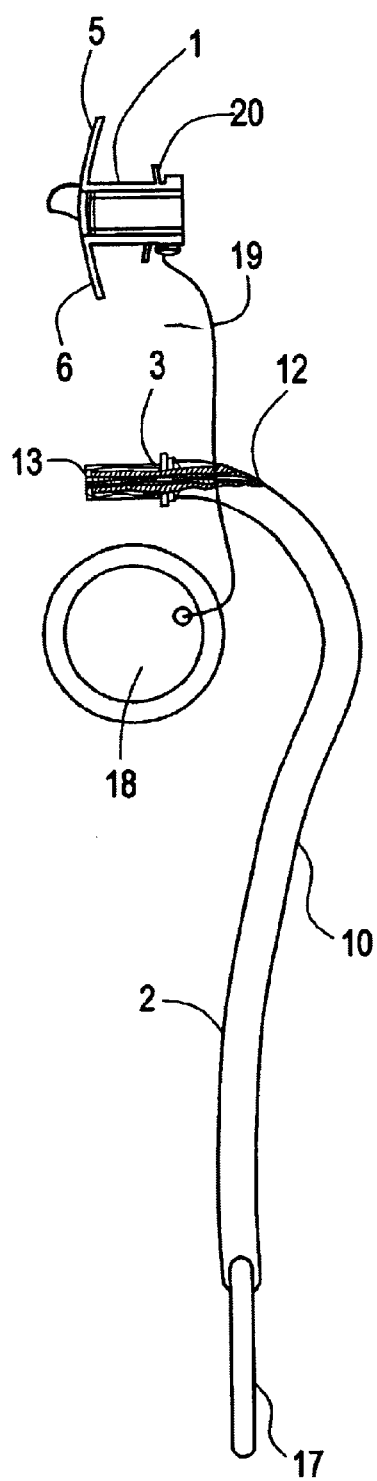
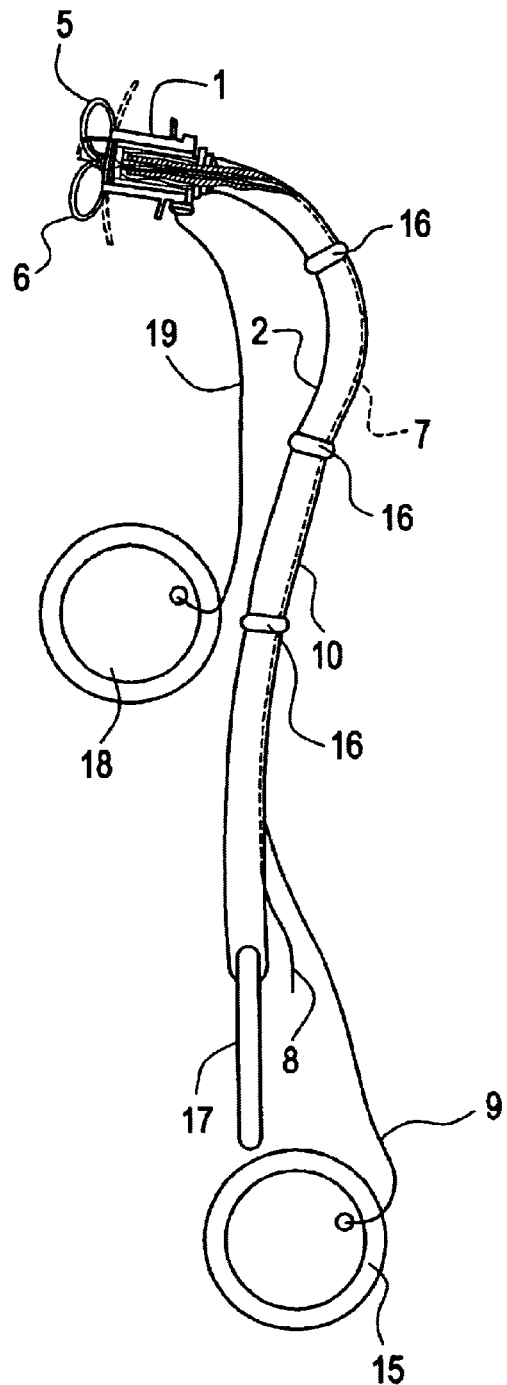

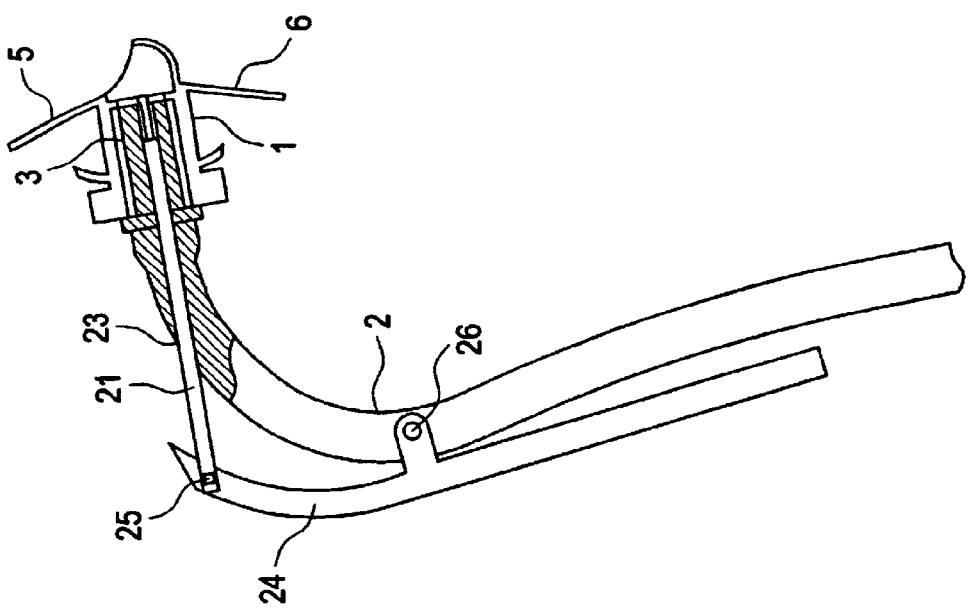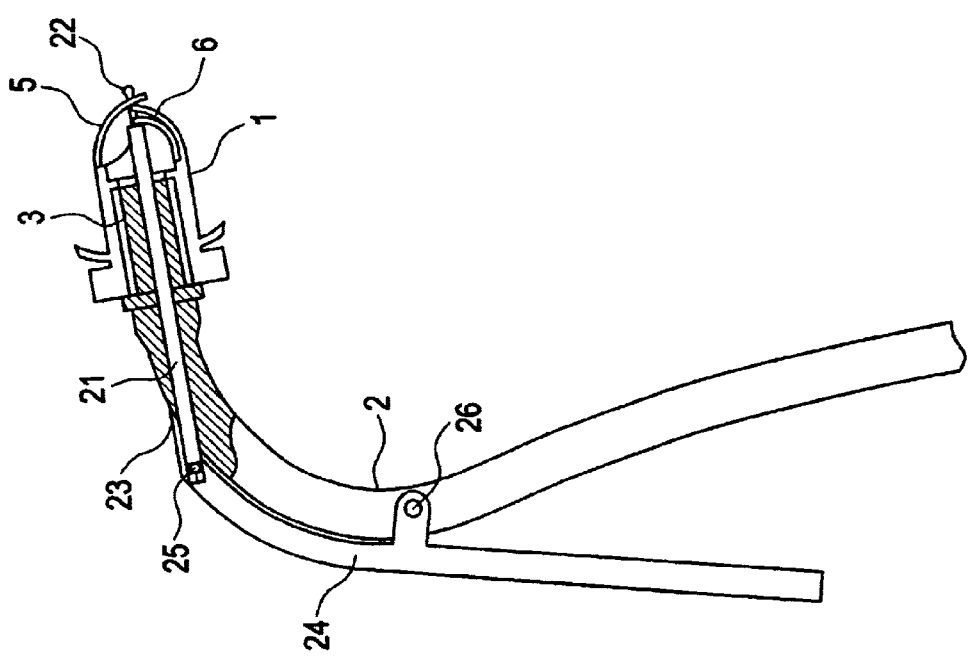

US 6,666,208 B1

SET FOR INSERTING A SHUNT VALVE INTO A SHUNT BETWEEN THE OESOPHAGUS AND THE TRACHEA

TECHNICAL FIELD

The invention concerns a set for the insertion of a shunt valve in a surgically created connecting channel (shunt) between trachea and oesophagus of a laryngectomized patient.

BACKGROUND OF THE INVENTION

The insertion of shunt valves has been known for a long time. A shunt valve of this kind is known, for example, from the applicant's recent German patent application 196 51 951. Usually the shunt valves have two circular flanges, of which one flange comes to lie on the oesophagus wall and the other flange comes to lie on the trachea wall after the insertion into the connecting channel.

Instead of the circular flange on the side of the esophagus, more recent developments have larger, more flexible holding straps, which quasi unfold in the radial direction after the insertion of the valve, and lie flush against the esophagus wall, in order thus to provide for a more sure hold of the valve in the connecting channel.

In this case the way in which a shunt valve with enlarged holding straps can be used at all in the connecting channel without being very unpleasant or even painful for the patient is a problem. Basically the main difficulty with the insertion of the valve into the connecting channel consists in rolling the flexible great holding straps which are separated from the main axis of the valve in a suitable way and letting them unfold only after the use of the valve.

Since this is not possible manually, an instrument or holder must be used for the shunt valve. A proposal to hold the above-mentioned holding straps in the rolled together condition during the insertion envisions holding the holding straps in the corresponding condition by means of a digestible adhesive. In the course of time after the insertion of the shunt valve the adhesive dissolves and the holding straps unfold in the envisioned way. However, the moment of the unfolding cannot be determined exactly, from which problems can develop.

SUMMARY OF THE INVENTION

Against this background, the object of the invention is to create a complete set for the insertion of a shunt valve, with which trouble-free insertion into the operatively created shunt is possible and which facilitates the process of insertion for the treating person.

The object is solved by the set according to claim 1. Advantageous further developments are cited in the subclaims.

In general a set for the insertion of a shunt valve in a surgically created connecting channel between the trachea and oesophagus of a laryngectomized patient is proposed, on the oesophagus side the shunt valve having at lest two flexible holding straps rolled together, which can be straightened out after the insertion in the connecting channel and lie against the oesophagus wall, having a holder with a proximal, essentially cylindrical coupling piece, on which the shunt valve is set, as well as a holding and releasing element, which holds the at least two holding straps capable of being related in the rolled together position and releases the holding straps for operation.

Accordingly, the essential feature of the invention is that the holding and releasing element is both the element which holds the at least two holding straps rolled together, as well as the element with which the unfolding of the holding straps is released in situ.

The concrete configuration of the invention is reflected in two embodiments described below.

According to a first preferred embodiment it is provided that the holding and releasing element is a guide rod with a spherical proximal end which can be moved, penetrating the essentially cylindrical coupling piece, which is capable of being set into the holding straps rolled together through openings and prevents the holding straps from unfolding without pulling, respectively pulling back, the guide rod.

This second embodiment is suited particularly for reusing, respectively for resupplying a patient, for example with a cleaned shunt valve in a medical practice. For this the physician can equip the instrument with a shunt valve in a simple way, roll up the indicated holding straps, and hold or stop the latter in their position by guiding the guide rod with its spherical end through the openings into the holding straps. The flexible material of the holding straps is stretched when the spherical end of the guide rod is guided through, so that the openings with small diameter in the holding straps are widened at the time of "loading" the instrument, and pulled back again, so that the rolled together holding straps are held in their position.

The release is achieved in the case of this second embodiment in a simple way by pulling on the back end of the guide rod, whereupon the spherical end of the guide rod passes through the openings in the holding straps with elastic widening of the material of the holding straps, and so the stopping action of the spherical end of the guide rod is ended. The elastic material of the shunt valve makes sure that at this moment the holding straps are unfolded in the way provided and described.

The use of the set according to this embodiment by the treating person corresponds to the use of the first embodiment of the set up to the release process.

According to a second preferred embodiment it is provided that the holding and release element is a pull thread with a first free end, which is guided along the holder to the coupling piece, emerges from the latter and which holds at least two holding straps releasably in the rolled together position, enters the coupling piece again, and is guided back along the holder, where it forms an operating end with its second free end.

In the case of this embodiment the release takes place in the simplest way by pulling on the operating end of the pull thread, whereupon the first free end of the thread is pulled in the direction to the coupling piece and the rolled together holding straps and from there back again in the direction of the coupling piece. If the pull thread was pulled so far on the operating end that the first free end of the pull thread has passed both holding straps, the flexible material of the holding straps is relaxed and the latter on the oesophagus side line against the oesophagus wall. The pull thread holds the holding straps in the rolled together condition essentially by the simple effect of friction. For this, the holding straps in each case can have a hole, through which the pull thread passes in each case.

The use of the set by the treating person takes place in the following way:

The treating person takes the sterile-packed set out of the packaging, and holds in one hand the ready-to-use set, which has the shunt valve with rolled-together holding straps ready to be inserted. The set is guided proximally through the tracheostoma on the connecting channel, the shunt valve is set with the rolled together holding straps through the channel until the valve has assumed the correct position. Then the person pulls on the operating end of the pull thread until the thread has been completely pulled out of the holder, so that in each case the holding straps can lie flush against the oesophagus wall and thus provide for a more secure hold.

According to an advantageous embodiment it is provided that the pull thread is guided along the back of the holder in a groove and by a guide hole at the height of the coupling piece in the latter, emerges at the end thereof, forms a loop passing through the holding straps, enters the hole again, and is guided down in the groove along the holder. By guiding the pull thread in the groove in the back, the pull thread is subject to a certain guiding. In addition the set can be made as a compact unit as a disposable article, without the pull thread being capable of being knotted or tangled detrimentally in use.

The last effect is supported advantageously by the fact that in the set according to a further development the pull thread is held in the groove holders surrounding the holder.

Advantageously the operating end of the pull thread is provided with a pull ring. This facilitates the operation of the set considerably, since the treating person only has to reach for the pull ring and does not have a difficult time finding the end of the pull thread.

Both embodiments described can be made advantageously so that the holder passes longitudinally stretched from the distal handle end and is bent into a bow to the proximal parts, then in order to pass out in the coupling piece or to end, the main axis of the coupling piece being at an angle between 70 to 90° to the longitudinal axis of the grip end. The shape of the holder facilitates the handling of the set, namely the proximal end on which the prepared shunt valve rests can be guided through the tracheostoma to the connecting channel between the trachea and esophagus. The bent shape also facilitates the visual monitoring by the treating person with respect to the correct guiding and position of the valve.

The embodiment with the holding and releasing element made as a guide rod according to the above-mentioned further development can be particularly preferably improved by means of the fact that the guide rod emerges on the back side from the above-mentioned bow and is hinged to an operating strap, which for its part is held capable of swiveling on the holder.

This simple mechanism permits easy handling of the set by the treating physician. In the loaded condition of the set, with shunt valve placed with the holding straps rolled together, the guide rod is pushed into its maximum displacement position. The swivel holding of the operating strap now is made so that, for example, the treating physician pushes on the end thereof, whereupon the operating strap is swiveled in such a way that the guide rod is pulled back out of this maximum position, the proximal spherical end—as described—with expansion of the material penetrates the openings in the holding straps, whereupon the holding straps unfold.

BRIEF DESCRIPTION OF THE PREFERRED EMBODIMENT

The invention is described in greater detail by means of two embodiments.

Figure 4:
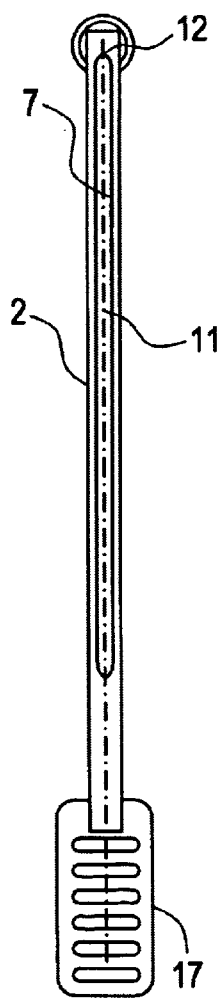

FIG. 1 Shows a side view of the main components shunt valve and holder of the set according to a first embodiment before the assembly, FIG. 2 shows the set in the inserted condition, FIG. 3 shows the proximal end of the set from FIG. 2, FIG. 4 shows the back view of the holder, FIG. 5 shows the side view of the set of another embodiment in the inserted condition, and FIG. 6 shows the set according to FIG. 5 after release.

DETAILED DESCRIPTION OF THE PREFERRED EMBODIMENT

In all drawing figures identical parts are provided with the same reference numbers. FIG. 1 shows the holder 2 of the set in a curved shape. In this case the holder 2 passes from the distal handle end 17 longitudinally stretched into a loop in its proximal end, which is formed by the coupling piece 3 with a face side 13.

The shunt valve 1 can be pushed onto the coupling piece 3. The shunt valve has a circular flange 20 and two radially projecting flexible holding straps 5 and 6. A ring 18, by means of which the valve 1 can be pulled out of the connecting channel between trachea and oesophagus as needed, is connected to the shunt valve 1 via a band 19.

The coupling piece 3 is penetrated by a hole 12, which opens in the area of the curved loop of the holder 2. At the time of the assembly of the set now the shunt valve 1 is set onto the coupling piece 3. Of course the pull thread 7 first must be inserted into the groove 11 on the back side in the back 10 of the holder, so that the one free end 8 of the pull thread 7 ends in the area of the handle end 17 and the thread 7 is set guided in the groove 11 through the hole 12. From the front side 13 of the coupling piece 3 the pull thread 7 emerges and forms a loop 14 here with penetration of the two holding straps 5 and 6 (FIG. 3). In this case a hole is made in each holding strap 5 and 6, through which the pull thread 7 is guided. Then the pull thread is set back into the hole 12 and guided down the holder 2 (FIG. 2). There its second free end 9 is provided with a pull ring 15, which facilitates the removal of the pull thread 7 from the holder 2.

The guiding of the pull thread 7 in the groove 11 of the holder 2 is stabilized by the holding pieces 16 surrounding the holder 2, which, for example can be formed by rubber rings.

In this way it is possible that the pull thread holder the rolled-together holding straps 5 and 6 in this condition.

FIG. 3 also shows as shaded the holding straps 5 and 6 after the unfolding, so that they can lie against the oesophagus wall in this condition. The trigger for this unfolding is—as explained—pulling on the pull thread 7 until the loop 14 is opened.

FIGS. 5 and 6 show another embodiment of the set. As opposed to the set according to the first embodiment, as described above, only the following are indicated below.

FIG. 5 shows the set of this embodiment in the "loaded" condition with the shunt valve 1 located on the cylindrical coupling piece 3. The holding straps 5 and 6 are presented folded together or rolled up and are presented held in this condition by the guide rod 21. The guide rod 21 proximally has a spherical end 22, which holds the holding straps 5 and 6 folded together. The material of the holding straps 5 and 6 is flexible, so that the spherical end 22 of the guide rod 21 can be pushed through the openings correspondingly made in the holding straps with expansion thereof.

The guide rod 21 passes through the cylindrical coupling piece 3 and is placed there movably.

In the area of the bow 23 the guide rod 21 emerges on the back side out of the holder 2. On its distal end the guide rod 21 is hinged to an operating strap 24, which for its part is hinged capable of swiveling in the holder 2 at 26, for example, by means of a pin 25.

FIG. 6 shows the set after releasing the operating strap 24. The treating physician has pushed the operating strap 24 in the direction to the holder 2, so that the front end of the operating strap 24 performs a corresponding swivel motion around 26. In this case the operating strap 24 carries with it the guide rod 21 hinged at 25, that is the guide rod 21 is pulled outside to a certain distance. In this case the spherical end 22 of the guide rod 21 passes through the openings in the holding straps 5 and 6, again with a slight widening of the dimensions of the openings. As soon as the holding straps 5 and 6 pass through the proximal end 22 of the guide rod 21, the holding straps 5 and 6 unfold—as shown in FIG. 6—because of the restoring forces which act.

The second embodiment can be reused in a simple way by the treating physician by a simple pushing of shunt valve 1 onto the cylindrical coupling piece 3 and subsequent folding of the holding straps 5 and 6 together and the proximal end 22 pushing through the openings into the holding straps 5 and 6.

What is claimed is:

1. A set for using a shunt valve in a connectinig channel produced surgically between the trachea and esophagus of a patient with a laryngectony, the set comprising:

at least two flexible retaining straps that are rolled together and can be aligned in the connecting channel after use and laid against an esophageal wall;

a holder with a coupling piece; and a hold and release element, which holds the at least two retaining straps in the rolled together position and releases the retaining straps when activated;

wherein the hold and release element is a guide rod that can move within the coupling piece and penetrates the coupling piece with a proximal spherical end, which runs through holes in the rolled-together retaining straps and keeps the retaining straps from unfolding until the is withdraw from the other.

2. The set according to claim 1, wherein the holder is stretched out alone, a longitudinal axis from a distal grip end and is curved in an arch at a proximal part, said holder extending into the coupling piece, whose main axis is at an angle between 70° and 90° to the longitudinal axis of the grip end.

3. The set according to claim 2, in which the guide rod comes out of the arch at a back portion and is coupled to an activating bracket which is rotatably connected to the holder.

* * * * *